US006217878B1

(12) United States Patent
Menon et al.

(10) Patent No.: US 6,217,878 B1
(45) Date of Patent: Apr. 17, 2001

(54) METHOD OF PREPARING ECHINACEA POWDER

(75) Inventors: Gopi R. Menon, Riverside; Ernesto Brovelli, Corona, both of CA (US); Jatinder Rana, Grand Rapids, MI (US); Yingqin Li, Murrieta, CA (US)

(73) Assignee: Amway Corporation, Ada, MI (US)

( * ) Notice: Subject to any disclaimer, the term of this patent is extended or adjusted under 35 U.S.C. 154(b) by 0 days.

(21) Appl. No.: 09/373,943

(22) Filed: Aug. 13, 1999

(51) Int. Cl.⁷ .................................................. A61K 35/78
(52) U.S. Cl. .............................................................. 424/195.1
(58) Field of Search ........................................... 424/195.1

(56) References Cited

U.S. PATENT DOCUMENTS

| | | | |
|---|---|---|---|
| 5,403,613 | * 4/1995 | Furui et al. | 426/599 |
| 5,578,307 | * 11/1996 | 'Wunderlich et al. | 424/195.1 |
| 5,656,310 | 8/1997 | Santilo, Jr. | |
| 6,008,249 | * 12/1999 | Gajdos et al. | 514/561 |
| 6,019,977 | * 2/2000 | Joseph | 424/195.1 |
| 6,027,757 | * 2/2000 | Menon | 426/443 |

FOREIGN PATENT DOCUMENTS 298 15 536 U * 12/1998 (DE).

OTHER PUBLICATIONS

ECHIPURE Product Literature.
Bauer, "The Echinacea Story—The Scientific Development of an Herbal Immunostimulant," Proceedings of Society for Economic Botany, London, Jul. 1–6, 1996, pp. 317–332 (1998) ("Abstract").
Bauer, R., "Echinacea: Biological Effects and Active Principles," ACS Symp. Ser., vol. 691, pp 140–57 (1998) ("Abstract").
Bauer, R., "HPLC Method on the Basis of Cichoric Acid and Alkamides for the Standardization of Echinacea Purpurea Preparations Prepared From Expressed Juice," Zeitschrift fur Phytothorapie, 18/5 (270–76) (1997) ("Abstract").

Bauer, "Echinacea Drugs—Effects and Active Ingredients," Zeitschrift fur Arztliche Fortbildung 90 (2) 111–5 (Apr. 1996) ("Abstract").
Sidorovich, "Diploid Form of Echinacea Purpurea—A New Source of Medicinal Raw Materials for Home–Produced Immunostimulating Preparations,"; Vest; Akademic Navuk Belarusi. Seriya Biyalaguchnykh Navuk, No. 2, pp. 5–7 (1997)("Abstract").
Blaschek, "Echinacea Polysaccharides: Analytical Investigations on Pressed Juice and the Preparation Echinacin," Zeitschrift fur Phytotherapie, 19/5 (255–62) (1998) ("Abstract").
Kurkin, "Quantitative Estimation of Total Hydroxycinnamic Acids in Aerial Part of Echinacea Purpurea," Rastitel'nye Resursy, vol. 34, No. 2 pp. 81–85 (1998) ("Abstract").
De Swaef, "Quantitative Determination of P–Coumaric Acid in Echinacea Purpurea Press juice and Urgenin," J. of Liquid Chromatography, vol. 17, No. 19., pp. 4169–4183 (1994) ("Abstract").
Facino, "Echinacoside and caffeoyl conjugates protect colagen from free radical–induced degradation," Planta Med., 61 (6): 570–4 (Dec. 1995).

* cited by examiner

*Primary Examiner*—Christopher R. Tate
(74) *Attorney, Agent, or Firm*—Warner Norcross & Judd LLP

(57) ABSTRACT

A process for producing an Echinacea powder having an increased amount of the cichoric acid present in the harvested Echinacea plant material. The process includes the following steps: 1) milling the harvested Echinacea plant material to reduce the particle size, 2) blanching the milled plant material, 3) recovering the juice from the blanched material, 4) concentrating the juice to have at least about a 20% soluble solids content, and 5) drying the juice to produce the Echinacea powder having a moisture content of less than about 8%. The blanching step enhances the juice recovery from the Echinacea plant material. The Echinacea powder can be tableted or combined with other nutrients in a dry supplement form.

20 Claims, 1 Drawing Sheet

METHOD OF PREPARING ECHINACEA POWDER

BACKGROUND OF THE INVENTION

The present invention relates to a method of producing a powder containing beneficial phytochemicals present in harvested Echinacea plant material, and more particularly to a method of producing a powder recovering an increased amount of the cichoric acid present in the harvested Echinacea plant material.

Echinacea plant is a popular herbal immunostimulant. Echinacea contains numerous active phytochemicals—such as caffeic acid derivatives (e.g., cichoric acid), alkamides (e.g., dodecatetraenoic acid isobutylamides), and glycoproteins/polysaccharides—that have immunomodulatory or other beneficial activity. Although cichoric acid is a particularly beneficial immunostimulant, it is advantageous to consume the full range of the phytochemicals present in Echinacea in order to gain the synergistically beneficial effect. The elimination of any one class of constituents could reduce this beneficial effect.

Accordingly, many people consume the freshly expressed juice of the Echinacea plant, which inherently contains the full spectrum of phytochemicals normally present in the Echinacea plant. For example, Europeans have consumed the freshly expressed juice of Echinacea, provided in vials or ampules, for many years. Representative of this type of product is the expressed juice of the flowering Echinacea purpurea plant harvested about 8 inches (20.3 cm) above the ground; this product has been sold since 1939 by Madaus Aktiengesellschaft under the ECHINACIN mark.

One drawback to Echinacea juice is that water is a major component. Water is a constituent lacking phytochemical activity. Yet water significantly increases the weight and volume of the Echinacea product—needlessly increasing the handling and shipping costs. Also, fresh Echinacea juice is not useable in dry, powdered dietary supplements.

Another drawback to Echinacea juice is that the water in the fresh juice provides an environment in which undesirable microbiological or enzymatic activity occurs. For example, R. Bauer reports that the content of cichoric acid varies dramatically from 0 to 0.4% in the expressed juice, in part from the inconsistent inhibition of the enzymatic degradation of cichoric acid in the freshly expressed juice. (Bauer, "HPLC-Method on the Basis of Cichoric Acid and Alkamides for the Standardization of Echinacea Purpurea Preparations Prepared from the Expressed Juice," Zeitschrift fur Phytotherapie 18/5, p. 270–276 (1997).) Therefore, in providing fresh juice, the manufacturer must either recommend relatively immediate consumption or otherwise treat the juice to reduce spoilage and enzymatic activity. One method of reducing the spoilage is to add alcohol to stabilize the juice. However, the alcohol may precipitate some beneficially active components of the juice, such as the polysaccharides. Alcohol also renders the product questionable for use with children.

Manufacturers have provided Echinacea extracts in powdered form to address the above-noted problems. However, many methods of producing the Echinacea powder—such as alcohol extraction followed by spray drying—may eliminate or damage many of the beneficial phytochemicals in the Echinacea juice and thus reduce the recovery of desired components such as cichoric acid. Accordingly, the amount of cichoric acid recovered in commercially available Echinacea extracts has been unacceptably low. Although Ital Nutritional, Inc. has supplied Echinacea juice in dried powder form having either 2.2% or 3.0% of total caffeic derivatives (e.g., cichoric acid, caeffoyl tartaric acid, caeffoyl quinic acid, and chlorogenic acid) as measured by the HPLC method, the process for converting the fresh Echinacea plant material to dried juice powder is relatively inefficient, about a 45:1 ratio for plant material feed to powdered final product.

SUMMARY OF THE INVENTION

The aforementioned problems are overcome in the present invention wherein an Echinacea powder is formed by blanching the expressed Echinacea juice before drying the juice to form the Echinacea powder. More specifically, the invention is directed to a method of producing a powder containing water-soluble solids of harvested Echinacea plant material. The harvested plant material is milled to reduce the plant particle size. The plant material is then blanched. The blanched material is expressed or squeezed to produce Echinacea juice. The juice is concentrated to at least about 20% soluble solids content. Then, the juice is dried to form an Echinacea powder having a moisture content of less than about 8%. Another aspect of the invention is an improved method of recovering juice from Echinacea plant material, in which the Echinacea plant material is blanched before squeezing the plant material to express the juice.

The inventive process has several advantages. The final Echinacea powder essentially reflects the full spectrum of phytochemicals present in the freshly expressed juice of Echinacea. Accordingly, the powder provides the full synergistic phytochemical effect available from consumption of fresh, expressed Echinacea juice. Yet the powder significantly reduces handling and shipping costs compared to Echinacea juice. Further, the powder produced by the inventive process has a vastly decreased microbiological and enzymatic activity in comparison to the expressed juice—without having to add alcohol or other components that may interfere or decrease the immunostimulatory effect of the Echinacea plant and increase the processing costs. Thus, the shelf life is markedly improved over fresh juice, so that the consumer can take the phytonutrients at a convenient time.

The Echinacea powder produced by the inventive process has high levels of cichoric acid, which is one of the particularly beneficial immunostimulatory phytochemicals in Echinacea. Further, the inventive process produces an increased juice yield from the Echinacea plant material. The dry Echinacea powder produced by the present invention can be tableted or combined with other nutrients in a dry supplement form. The inventive powder has been observed to induce the activity of Phase II enzymes, which have a detoxifying effect on potential carcinogens in the human body. This inductive effect is comparable to that of broccoli, which is an extensively documented vegetable having cancer chemopreventative function.

These and other objects, advantages, and features of the invention will be more readily understood and appreciated by reference to the detailed description of the preferred embodiment and the drawings.

DETAILED DESCRIPTION OF THE PREFERRED EMBODIMENT

Figure 1:
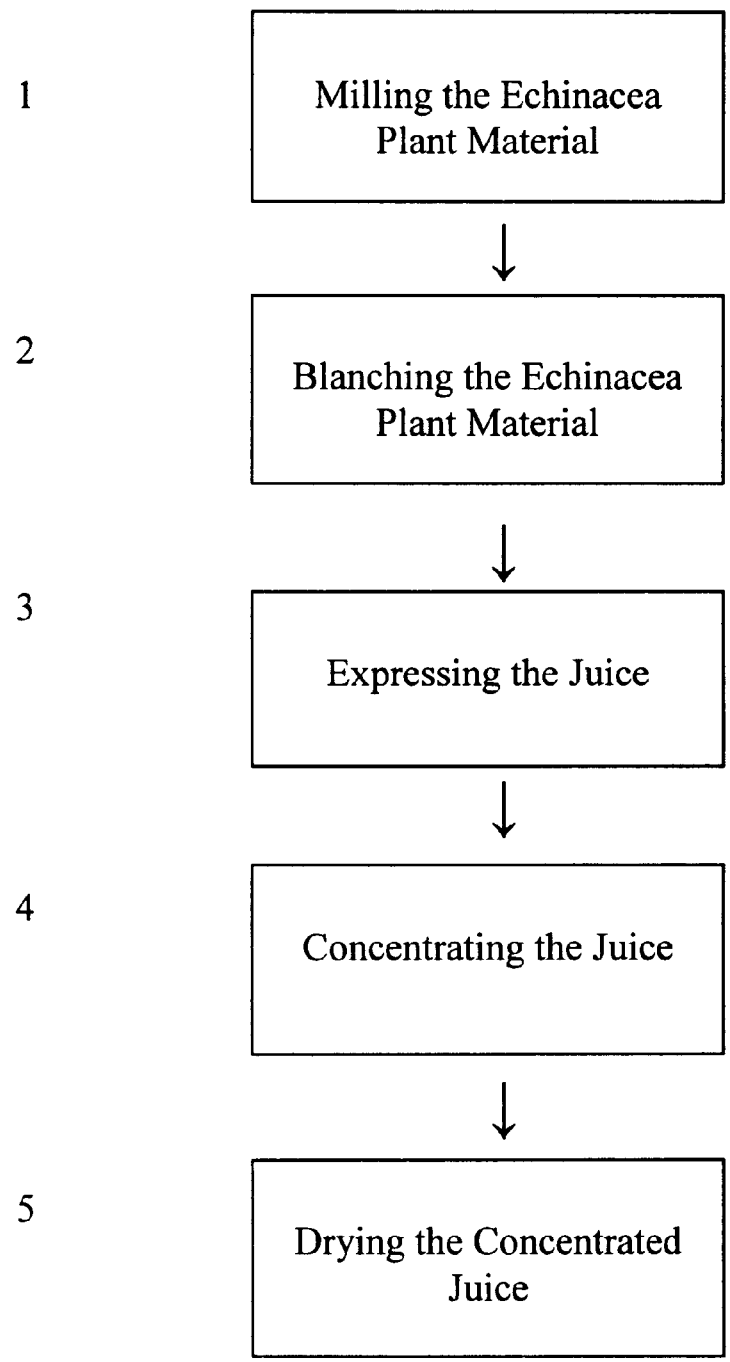
FIG. 1 is a flow chart showing the steps of the present invention.

The inventive process for producing Echinacea juice powder is shown generally in FIG. 1, and includes a blanching step 3 to enhance the powder yield. In the preferred embodiment, the process includes the following steps: 1) milling the Echinacea plant material, 2) blanching the milled plant material, 3) recovering the juice from the blanched material, 4) concentrating the juice, and 5) drying the juice to produce a powder.

Echinacea Feedstock

The process of the present invention is suitable for any Echinacea species. It is believed that Echinacea purpurea, and especially the tops of *E. purpurea,* provides the highest concentration of desirable components, such as cichoric acid and polysaccharides. Preferably, the Echinacea is organically grown and harvested when the crop has bloomed with: 1) more than 50% of the flowers being fully developed (i.e., the petals are totally colored and may be droopy or spreading, with the central disk having a conical shape and the bristles having a deep orange color), 2) no more than 10% of the flowers being senescent, and 3) between about 10 to 25% of the flowers in the developing stage. Also preferably, the plants are harvested at least about 3 inches (7.62 cm) above the ground.

Milling the Echinacea Plant Material

Turning to step 1, the Echinacea plant material is milled, ground, or chopped to produce milled plant material having a particle size effective to increase the subsequent juice recovery in comparison to a non-milled plant material. Preferably the milling step produces milled plant particles having an average length of less than about 2 inches (5.1 cm), more preferably particles of which a substantial portion has a length of from about 0.25 inch (0.64 cm) to about 2 inches (5.1 cm) in length. Suitable machines for chopping the Echinacea plant material include: i) an Urschel chopper (Comitrol) having a 0.24 inch (0.61 cm) mill head and ii) a GoodNature EG400/50 Crop Chopper. Methods of milling or grinding plant materials are described in U.S. Pat. No. 5,565,310 issued Aug. 12, 1997 to Santillo entitled "Process for Producing a Powdered Food Supplement," which is incorporated herein in its entirety by this reference.

Blanching the Echinacea Plant Material

Turning to step 2, the milled Echinacea tops are blanched, preferably by steam blanching. The Echinacea plant material is preferably blanched under conditions and for an amount of time effective to enhance the juice recovery—that is, an amount of time effective to increase the yield of juice in subsequent operations when compared to the same operation without the blanching step, preferably at least about a 12% increase in yield, more preferably about a 17% increase in yield. The blanching step deactivates the enzymes and softens the Echinacea plant to help increase the subsequent juice yield. Further, the blanching can help reduce microbiological activity, preferably to an aerobic plate count ("APC") of less than about 10,000 colony forming units ("CFU") more preferably less than about 3,000 CFU. Effective blanching conditions include blanching for at least 1 minute at a temperature of 180° F. (82° C.), preferably at least about 2 minutes, and more preferably from about 2 minutes to about 2.5 minutes at steam temperature of 212° F. (100° C.). Methods of blanching vegetables and the related blanching equipment are known to those of skill in the art; see, for example, U.S. Pat. 5,403,613 issued Apr. 4, 1995 to Furui entitled "Method of Producing Carrot Juice," which is incorporated herein in its entirety by this reference.

Expressing the Juice

Turning to step 3, the juice is expressed or "juiced" from the blanched plant material. To express the juice, the blanched material is squeezed or pressed by any of a number of methods known in the art, such as a screw press, hydraulic press, or juicer. Preferably the juice is expressed by feeding the blanched plant material to a high efficiency press, such as a hydraulic press. For example, the blanched material may be cooled to about 140° F. (60° C.)and squeezed under a pressure of at least about 80 psig (552 kPa) to about 100 psig (689 kPa) in a hydraulic press, such as that available from GoodNature Products, Inc. Of Buffalo, N.Y. Preferably, the squeezing pressure is sufficient to produce at least about 40%, more preferably about 50%, and most preferably at least about 55%, juice by weight of the blanched material (e.g., at least about a 2:1 extract ratio of fresh plant to expressed juice). The resultant pressed cake will preferably have less than about 65% moisture. The resulting expressed Echinacea juice may have soluble solids content of at least about 4% solids, typically in the range of from about 7% to about 12% solids.

Concentrating the Juice

Turning to step 4, the expressed juice may be concentrated by removing a first portion of water to form a concentrated juice having an increased soluble solids content, preferably, a soluble solids content of at least about 20%, more preferably at least about 25%; and in the range of from about 20% to about 35%, more preferably from about 25% to about 30%. The first portion of water can be removed, for example, by passing the juice through a vacuum evaporator (e.g., a Turba-Film evaporator) operating at or less than about 135° F. (57° C.) and 27 inches Hg vacuum (91 kPa).

A carrier may be added to the concentrated juice in an amount effective to help prevent sticking during the subsequent drying step. Suitable carriers, such as maltodextrin and tricalcium phosphate, are known to those of skill in the art. Preferably the carrier is a non-hygroscopic material, such as tricalcium phosphate, so that the dried juice powder may be tableted, if desired, without subsequent significant absorption of water from the atmosphere. Effective amounts of carrier may depend on the amount of soluble solids present; effective ratios of carrier to soluble solids include from about 0.2:1 to about 1.2:1, more preferably from about 0.25:1 to about 1:1, even more preferably about 0.25:1.

The concentrated expressed juice may also be heat treated to further stabilize the concentrated juice, for example, to further reduce the microbiological or enzymatic activity. One method is to pasteurize the concentrated juice, for example, by exposing the concentrated juice to from about 180° F. to about 240° F. (i.e., 82° C. to 116° C.)for from about 30 seconds to about 3 minutes.

If a choice must be made between incorporating a processing delay at the expressed juice stage (e.g., by storing or transporting the expressed juice) and a processing delay at the concentrated juice stage (e.g, by storing or transporting the concentrated juice), it was found that the cichoric acid content in the final powder is higher if the delay takes place at the expressed juice stage.

Drying the Concentrated Juice

Turning to step 5, the pasturized, concentrated juice is then dried to produce a dried powder having a moisture content of less than about 8%, preferably less than about 5%. The concentrated juice can be dried by any of a number of methods, for example, by use of a spray dryer, vacuum dryer, or tray dryer. A preferred method is spray drying, with an inlet temperature of from about 300° F. to about 330° F. (149° C. to 166° C.)and an outlet temperature of from about 200° F. about 220° F. (93° C. to 104° C.). The dried particles are such that preferably a maximum of 40% of the particles can pass through a 100-mesh screen and at least 100% of the particles can pass through a 16-mesh screen.

The resulting dried Echinacea juice powder has a cichoric acid content of at least about 1.5%, more preferably at least about 2% cichoric acid, still more preferably at least about 3.5%, and even more preferably at least about 4%.

The powder formed by the present invention can be consumed orally to enhance the body's immunological response. The powder can also be tableted or combined with other herbal constituents in a blended supplement.

The following examples are presented for the purpose of further illustrating and explaining the present invention and are not to be taken as limiting in any regard. Unless otherwise indicated, all parts and percentages are by weight.

EXAMPLE 1

The aerial parts of Echinacea purpurea plant —namely, the flowers, stems, and other top parts (i.e., "tops")—were harvested during June from plants grown at the Lake view, Calif. farm of the Nutrilite Division of Amway Corporation. The plant material was chopped using a Urschel chopper having a 0.24 inch (0.61 cm) mill head to produce 100.65 kg of chopped plant material having a moisture content of 76.4%. The chopped plant material was blanched for 2 minutes with steam at 212° F. (100 °C.) to produce 113.91 kg of blanched plant material having a 77.30% moisture content The blanched material was juiced in a hydraulic press to form 56.6 kg of juice having 9.0% soluble solids content and 49.55 kg of cake having 36.6% solids. The expressed juice was concentrated to 14.8 kg by vacuum evaporation to produce a concentrate having a 30.8% soluble solids content (i.e., 4.56 kg soluble solids).

To this concentrate, four different carrier systems were added before pasteurization at 180° F. (82° C.)for 3 minutes. The pasteurized concentrate was spray-dried at about 310° F. (154° C.)inlet and about 200° F. (93° C.)outlet conditions to produce powdered juice extracts having the cichoric acid amounts and the ratios of plant material feed to final dried product noted below.

|  | Example 1A | Example 1B | Example 1C | Example 1D |
| --- | --- | --- | --- | --- |
| Carrier System | Maltodextrin at 25% of solids | Maltodextrin at 50% of solids | Tricalcium Phosphate at 25% of solids | Tricalcium Phosphate at 50% of solids |
| Carrier Added (kg) | 1.1396 | 2.2792 | 1.1396 | 2.2792 |
| Total Soluble Solids (kg) before drying | 5.698 | 6.8376 | 5.698 | 6.8376 |
| Total Soluble Solids (kg) after drying | 4.5584 | 6.017 | 4.5584 | 5.7436 |
| Wt Ratio of Chopped Plant Material to Dried Juice Powder | 22.1:1 | 16.7:1 | 22.1:1 | 17.5:1 |
| Cichoric Acid in the Dried Powder (%) | 3.67% | 2.95% | 4.31% | 3.69% |

EXAMPLE 2

The aerial parts of Echinacea purpurea plant (but without flowers) were harvested during October from plants grown at the Lake view, Cal. farm of the Nutrilite Division of Amway Corporation. The plant material was chopped using a Urschel chopper having a 0.24 inch (0.61 cm) mill head to produce 130.85 kg of chopped plant material having a moisture content of 75.0%. The chopped plant material was blanched for 2.5 minutes with steam at 212° F. (100° C.) to produce 148.75 kg of blanched plant material having a 77.50% moisture content. The blanched material was juiced in a hydraulic press to form 60.35 kg of juice having 10.6 % soluble solids content and 78.05 kg of cake having 36.6% solids. The expressed juice was concentrated to 18.8 kg by vacuum evaporation to produce a concentrate having a 32.15 % soluble solids content (i.e., 6.04 kg soluble solids).

To this concentrate, two different carrier systems were added before pasteurization at 180° F. (82° C.)for 3 minutes. The pasteurized concentrate was spray-dried at about 310° F. (154° C.)inlet and about 200° F. (93 °C.) outlet conditions to produce powdered juice extracts having the cichoric acid amounts and the ratios of plant material feed to final dried product noted below.

|  | Example 2A | Example 2B |
| --- | --- | --- |
| Carrier System | Maltodextrin at 25% of solids | Tricalcium Phosphate at 25% of solids |
| Carrier Added (kg) | 1.511 | 1.5111 |
| Total Soluble Solids (kg) before drying | 7.555 | 7.555 |
| Total Soluble Solids (kg) after drying | 6.422 | 6.724 |
| Wt Ratio of Chopped Plant Material to Dried Juice Powder | 20.4:1 | 19.5:1 |
| Cichoric Acid in the Dried Powder (%) | 1.60% | 1.70% |

The above descriptions are those of preferred embodiments of the invention. Various alterations and changes can be made without departing from the spirit and broader aspects of the invention as defined in the claims, which are to be interpreted in accordance with the principles of patent law, including the doctrine of equivalents. Except in the claims and the specific examples, or where otherwise expressly indicated, all numerical quantities in this description indicating amounts of material, reaction conditions, use conditions, and the like, are to be understood as modified by the word "about" in describing the broadest scope of the invention. Any reference to an item in the disclosure or to an element in the claim in the singular using the articles "a," "an," "the," or "said" is not to be construed as limiting the item or element to the singular unless expressly so stated.

The embodiments of the invention in which an exclusive property or privilege is claimed are defined as follows:

1. An improved method of recovering juice from Echinacea plant material by squeezing the Echinacea plant material to express the juice, wherein the improvement comprises steam blanching the Echinacea plant material before the squeezing step.

2. The method of claim 1 further comprising milling the Echinacea plant material to form Echinacea plant particles having a length of less than about 2 inches (5.1 cm) before the steam blanching step.

3. The method of claim 1 wherein the steam blanching step includes heating the Echinacea plant material to a temperature of at least 180° F. (82° C.) for at least about 1 minute.

4. The method of claim 3 wherein the steam blanching step includes steam blanching for at least about 2 minutes.

5. The method of claim 1 wherein the squeezing step applies a pressure sufficient to produce Echinacea juice in an amount of at least about 40% of the weight of the steam blanched Echinacea plant material.

6. A method of producing a powder containing water-soluble solids of harvested Echinacea plant material comprising:

milling the Echinacea plant material to produce a milled plant material having a reduced particle size;

steam blanching the milled plant material to produce a blanched plant material;

expressing the blanched plant material to produce juice;

concentrating the juice to produce a juice concentrate having at least about 20% soluble solids content; and drying the juice concentrate to produce an Echinacea powder having a moisture content of less than about 8%.

7. The method of claim 6 wherein the juice concentrate is dried to form a powder having a cichoric acid content of at least about 1.5%.

8. The method of claim 6 wherein the juice concentrate is dried to form a powder having a cichoric acid content of at least about 3.5%.

9. The method of claim 6 wherein the steam blanching step occurs at a temperature of at least about 180° F. (82° C.) and for a duration of at least 1 minute.

10. The method of claim 9 wherein the steam blanching step includes steam blanching for a duration of at least 1 minute.

11. The method of claim 6 further comprising allowing the juice to rest for at least 6 hours before the concentrating step.

12. The method of claim 6 wherein the expressing step includes pressing the steam blanched plant material to produce Echinacea juice in an amount of at least about 40% of the weight of the blanched plant material.

13. The method of claim 6 wherein the expressing step includes pressing the steam blanched plant material to produce Echinacea juice in an amount of at least about 50% of the weight of the blanched plant material.

14. The method of claim 6 wherein the concentration step includes vacuum evaporation.

15. The method of claim 6 further comprising adding a carrier to the concentrated juice in an amount effective to reduce the loss of soluble solids during the subsequent drying step.

16. The method of claim 15 wherein the carrier is added in an amount of between about 25% and about 100% of the soluble solids present in the juice concentrate.

17. The method of claim 6 further comprising pasteurizing the juice concentrate before the drying step.

18. The method of claim 6 wherein the drying step includes spray drying.

19. The method of claim 18 wherein the inlet temperature of the spray dryer is from about 300° F. (149° C.) to about 330° F. (166° C.) and the outlet temperature is from about 200° F. (93° C.) to about 220° F. (104° C.).

20. A method of producing a powder containing water-soluble solids of harvested Echinacea plant material comprising:

milling the Echinacea plant material to produce a milled plant material having a reduced particle size;

steam blanching the milled plant material at a temperature of at least about 180° F. (82° C.) and for a duration of at least 1 minute to produce a blanched plant material;

pressing the blanched plant material to produce juice in an amount of at least about 40% of the weight of the blanched plant material;

concentrating the juice to produce a juice concentrate having at least about 20% soluble solids content;

pasteurizing the juice concentrate to produce a pasteurized juice; and spray drying the pasteurized juice to produce an Echinacea powder having a moisture content of less than about 8% and a cichoric acid content of at least about 3%.

* * * * *